United States Patent [19]

Specht

[11] Plant 4,145

[45] Nov. 8, 1977

[54] MAGNOLIA TREE

[75] Inventor: Carl H. Specht, North Salem, N.Y.

[73] Assignee: Brooklyn Botanic Garden Corporation, Brooklyn, N.Y.

[21] Appl. No.: 741,800

[22] Filed: Nov. 15, 1976

[51] Int. Cl.[2] ..... A01H 5/00

[52] U.S. Cl. ..... Plt./51

[58] Field of Search ..... Plt./51

*Primary Examiner*—Robert E. Bagwill

*Attorney, Agent, or Firm*—Brumbaugh, Graves, Donohue & Raymond

[57] ABSTRACT

A magnolia tree characterized by distinctive flowers, the tepals of which are a clear yellow with the outermost whorl slightly tinged with green.

1 Drawing Figure

1

This invention relates to a new variety of magnolia tree which has resulted from the crossing of *Magnolia acuminata* L., naturally occurring from New York to Georgia and west to Illinois and Arkansas, with *M. denudata* Desrouss., a native of China.

The distinctive characteristics of this new variety of magnolia tree are the unique form and coloration of the flowers. More specifically, the tepals of the flowers in the mature state are of a yellow color, the clarity and tonal uniformity of which distinguishes them from known magnolia species or varieties.

The flower of the magnolia tree of this invention is shown in the accompanying photographic color reproduction.

The deciduous tree of the present invention is presently growing on the grounds of the Kitchawan Research Station of the Brooklyn Botanic Garden in Westchester, N. Y. and is designated by the number "391". The tree is 19 years old and stands 5½ meters high and originated as a seedling from a number of crosses between *Magnolia acuminata* (female parent) and *M. denudata* (male parent). The tree first came into flower in 1972. The seeds from which the tree was selected were germinated at Brooklyn Botanic Garden, New York, and the seedlings were grown on at the Kitchawan Research Station.

The tree, which is pyramidal in form, is much branched and consists of two trunks. Bark of the older branches is smooth and grey with conspicuous lenticels. Leaves are generally obovate with cuspidate apices, cuneate to rounded leaf bases and entire margins. They measure 12–23 cm. in length, 7–20 cm. in width with hairs concentrated on the veins. The upper surface is bright green with hairs confined to the mid-vein alone. Tomentose stipules are present on the youngest shoots and are adnate to the petiole. These are early deciduous and leave a scar after detachment. The vegetative buds are 7–10 mm. long. Flower buds are larger and broader and reach a length of 25–35 mm. A glabrous, brown, spathe-like bract which is dry and papery by the time the bud reaches maturity, covers the perianth and eventually splits along one side as the bud swells.

Pedunculate flowers are produced singly at the end of the shoot and flowering coincides with the early unfurling of the new leaves.

The distinctive characteristics of the flower of this magnolia tree are described below by reference to the color code of the Royal Horticultural Society Color Chart, 1966.

2

As soon as the bract is sloughed off, the outermost whorl of tepals show a shading from a Yellow-Green 149A at the base, accentuated along the veins, through a Yellow-Green 154C in the center of the tepal to a Yellow 5D at the tip. This overtone of green becomes less prominent as the bud opens and the tepals take on a uniform hue corresponding to Yellow 9D when viewed from the outside of the flower. On looking down into the open flower, the predominant color is a translucent yellow with a tinge of green, corresponding to Yellow-Green 150D. This clarity and evenness of yellow coloration is unique among magnolias presently described.

With regard to shape, the newly opened flower holds its form well for the first day or two but the flower soon opens widely displaying the subtle yellow-green tones. However, the greenness is not as pronounced as in the flower of the female parent, *Magnolia acuminata.* Also, the heavy, farinaceous overlay in the tepals of this parent is absent in the hybrid. Each of the tepals is spathulate with broad, rounded tip, 7–9 cm. in length and 2.5–5.0 cm. in width. At maturity, when still campanulate in form, the flower measures up to 8 cm. across. As the flower opens, the tepals are shown to be undulate. Stamens are a rich yellow while the stigmas are paler. Pedicels are green and are up to 1 cm. long.

It appears that the leaf form, flower shape and texture of the tepals has been inherited from the male parent, *Magnolia denudata.* While the definite yellow tone of the tepals is shared with the female parent, *M. acuminata,* the bluish greens present in the outer tepals of this parent are not nearly as pronounced in the new magnolia. Whereas the flowers in *M. acuminata* open when the leaves are fully expanded, the new magnolia shares the characteristic of flowering before full leaf development with *M. denudata.*

On the basis of flowering dates taken during 1975, the blooming period in Westchester of the new magnolia averages 16 days, from May 7 to May 22 inclusive.

The tree of the present invention was first asexually reproduced at the Kitchawan Research Station in 1975 by taking softwood cuttings in July. These cuttings were treated with hormone powder and rooted under mist in a mixture of Terralite, peat and Perlite. Rooting occurred after 25 to 35 days.

I claim:

1. A new and distinct variety of magnolia tree as herein described and illustrated, characterized by the tepals of the flower being a clear yellow with the outermost whorl slightly tinged with green.

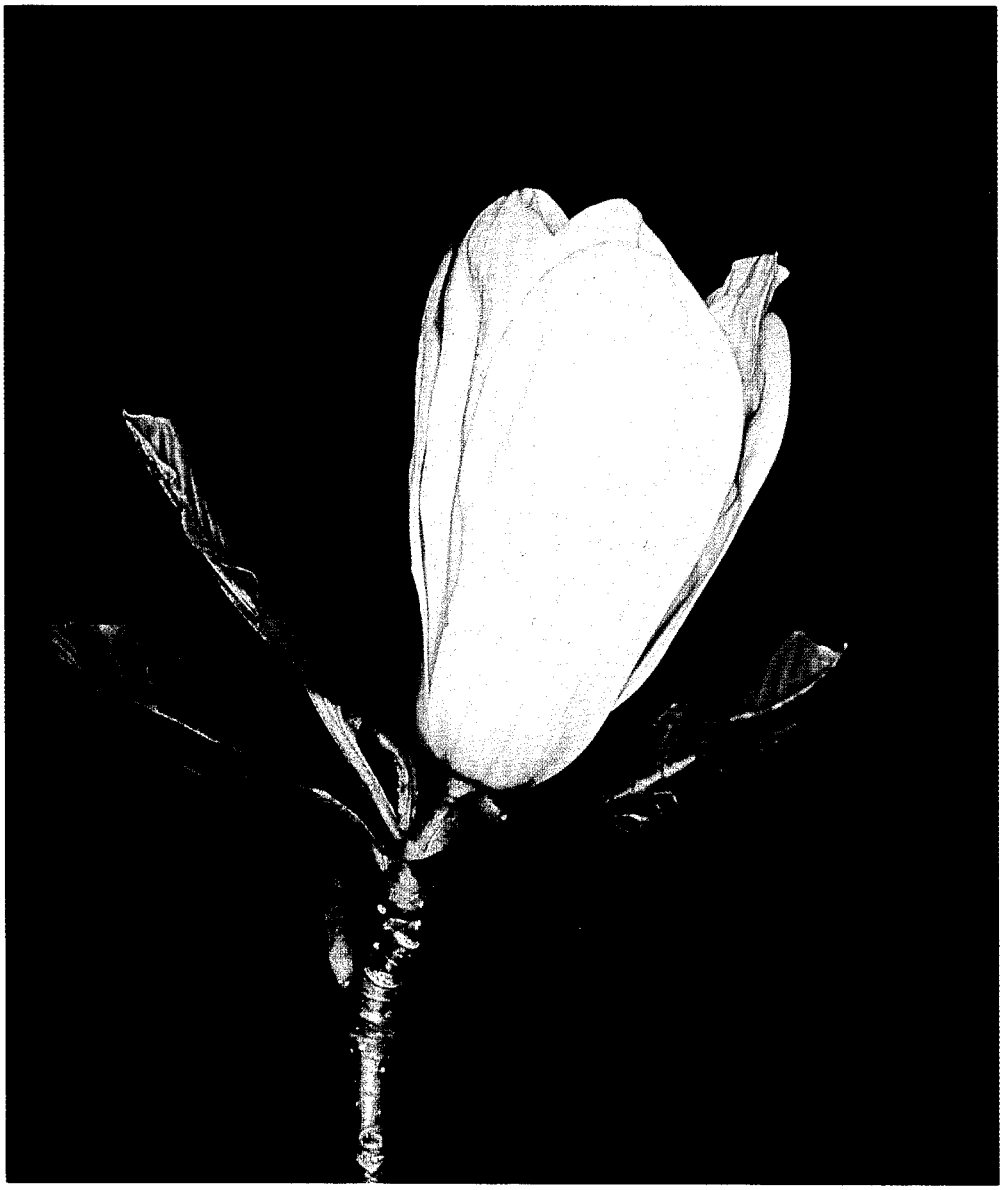

* * * * *